(12) United States Patent
Brown et al.

(10) Patent No.: US 11,680,873 B2
(45) Date of Patent: Jun. 20, 2023

(54) SAMPLING APPARATUS AND METHOD

(71) Applicant: Cargill, Incorporated, Wayzata, MN (US)

(72) Inventors: Ted Brown, Haven, KS (US); Tyson Brown, Wichita, MD (US)

(73) Assignee: CARGILL, INCORPORATED, Wayzata, MN (US)

( * ) Notice: Subject to any disclaimer, the term of this patent is extended or adjusted under 35 U.S.C. 154(b) by 108 days.

(21) Appl. No.: 16/756,942

(22) PCT Filed: Oct. 18, 2018

(86) PCT No.: PCT/US2018/056465
§ 371 (c)(1),
(2) Date: Apr. 17, 2020

(87) PCT Pub. No.: WO2019/079563
PCT Pub. Date: Apr. 25, 2019

(65) Prior Publication Data
US 2021/0199541 A1 Jul. 1, 2021

Related U.S. Application Data

(60) Provisional application No. 62/574,478, filed on Oct. 19, 2017.

(51) Int. Cl.
*G01N 1/02* (2006.01)
*G01N 33/02* (2006.01)

(52) U.S. Cl.
CPC ............... *G01N 1/02* (2013.01); *G01N 33/02* (2013.01); *G01N 2001/028* (2013.01)

(58) Field of Classification Search
CPC ..... G01N 1/02; G01N 33/02; G01N 2001/028
See application file for complete search history.

(56) References Cited

U.S. PATENT DOCUMENTS

| | | |
|---|---|---|
| 2,810,944 A | 10/1957 | Sander |
| 2,973,131 A | 2/1961 | Mead |
| 5,022,530 A | 6/1991 | Zieke |
| 5,138,750 A | 8/1992 | Gundlach |
| 5,301,806 A * | 4/1994 | Olson ............... A41D 19/0068 15/227 |
| 5,372,428 A | 12/1994 | Bruno |
| 5,435,844 A | 7/1995 | Sasaya |

(Continued)

FOREIGN PATENT DOCUMENTS

| | | |
|---|---|---|
| CN | 202624867 U | 12/2012 |
| CN | 203652289 U | 6/2014 |

(Continued)

*Primary Examiner* — Natalie Huls (57) ABSTRACT

Sampling of food products and/or surfaces can be efficiently carried out by providing an apparatus comprising a bag construction incorporating a sample collection material secured to an inside surface of the bag. The bag is of a size large enough to permit inversion of the bag to expose the sample collection material for collection of samples from surfaces, followed by re-inversion to enclose the sample collection material. Methods for sampling food products and/or surfaces for detection of pathogens, microbial contaminants and/or constituents in products or on surfaces are additionally contemplated.

16 Claims, 7 Drawing Sheets

(56) References Cited

U.S. PATENT DOCUMENTS

| | | | | |
|---|---|---|---|---|
| 5,833,058 | A | * | 11/1998 | Mabry ................ B65D 81/264 206/204 |
| 6,004,032 | A | | 12/1999 | Kapperman |
| 6,024,094 | A | | 2/2000 | Utecht |
| 6,383,804 | B1 | | 5/2002 | Ward, Jr. |
| 6,539,549 | B1 | * | 4/2003 | Peters, Jr. .......... A41D 19/0075 15/227 |
| 9,151,005 | B1 | * | 10/2015 | Hao .................... A01K 13/001 |
| 10,955,314 | B1 | * | 3/2021 | Emanuel .................. G01N 1/02 |
| 2013/0118275 | A1 | | 5/2013 | Lafond |
| 2014/0165746 | A1 | * | 6/2014 | Webb ................ B65D 33/2516 73/864.51 |
| 2015/0241401 | A1 | | 8/2015 | Wu |
| 2015/0301043 | A1 | * | 10/2015 | Price ....................... G01N 1/04 73/864.31 |
| 2016/0296211 | A1 | * | 10/2016 | Luffman ................ B01L 3/505 |
| 2017/0096278 | A1 | | 4/2017 | Salazar |

FOREIGN PATENT DOCUMENTS

| | | | |
|---|---|---|---|
| CN | 103228359 | B | 2/2015 |
| CN | 205658926 | U | 10/2016 |

\* cited by examiner

SAMPLING APPARATUS AND METHOD

CROSS REFERENCE TO RELATED APPLICATIONS

This application is a national phase application of PCT/US2018/056465, filed 18 Oct. 2018, entitled SAMPLING APPARATUS AND METHOD, which claims the benefit of priority to U.S. Provisional Application No. 62/574,478, filed 19 Oct. 2017, entitled SAMPLING APPARATUS AND METHOD, which are hereby incorporated by reference in their entirety.

FIELD

The present invention relates to systems for sampling food products and methods for using same.

BACKGROUND

Food product sampling has been carried out for many years to determine whether the food contains pathogens, microbial contaminants and/or constituents in products. U.S. Pat. No. 2,973,131 describes bags for liquid such as milk and more particularly to bags which may be utilized in securing samples of milk and the like, as for test purposes. Other food sampling constructions are described in US Patent Application Publication No. 2013/0118275 A1 to Laford and in US Patent Application Publication No. 2015/0241401 A1 to Wu.

SUMMARY

It has been found that sampling of food products and/or surfaces can be efficiently carried out by providing an apparatus comprising a bag construction incorporating a sample collection material secured to an inside surface of the bag. The bag is of a size large enough to permit inversion of the bag to expose the sample collection material for collection of samples from surfaces, followed by re-inversion to enclose the sample collection material.

The apparatus is thus an all-in-one sampling kit that reduces the possibility of cross contamination and to reduce consumables per sample. Because the sample collection material is secured to an inside surface of the bag, the person charged with collection of the sample is less likely to drop and thereby contaminate the sample. Access to the sample collection material for sample collection is carried out in a two-handed operation while easily avoiding cross contamination of the sample by inversion of the bag. After collection of the sample, the sample collection material can be returned to the inside of the bag by re-inversion of the bag, which can then form a secure enclosure for the sample. Because the sample collection material is secured to an inside surface of the bag, there is no need to find a way to hold the bag open to insert a sample collection material.

BRIEF DESCRIPTION OF THE DRAWINGS

The accompanying drawings, which are incorporated in and constitute a part of this application, illustrate several aspects of the invention and together with a description of the embodiments serve to explain the principles of the invention. A brief description of the drawings is as follows.

DETAILED DESCRIPTION

The aspects of the present invention described below are not intended to be exhaustive or to limit the invention to the precise forms disclosed in the following detailed description. Rather a purpose of the aspects chosen and described is by way of illustration or example, so that the appreciation and understanding by others skilled in the art of the general principles and practices of the present invention can be facilitated.

Figure 1:
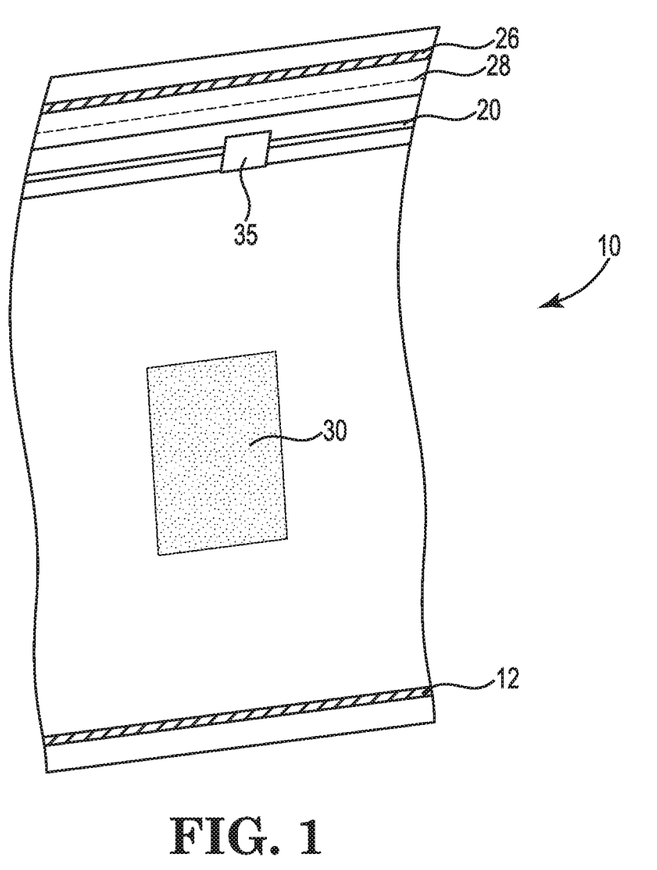
FIG. 1 is a perspective view of an aspect of a bag of the present invention having a top seal.
Figure 2:
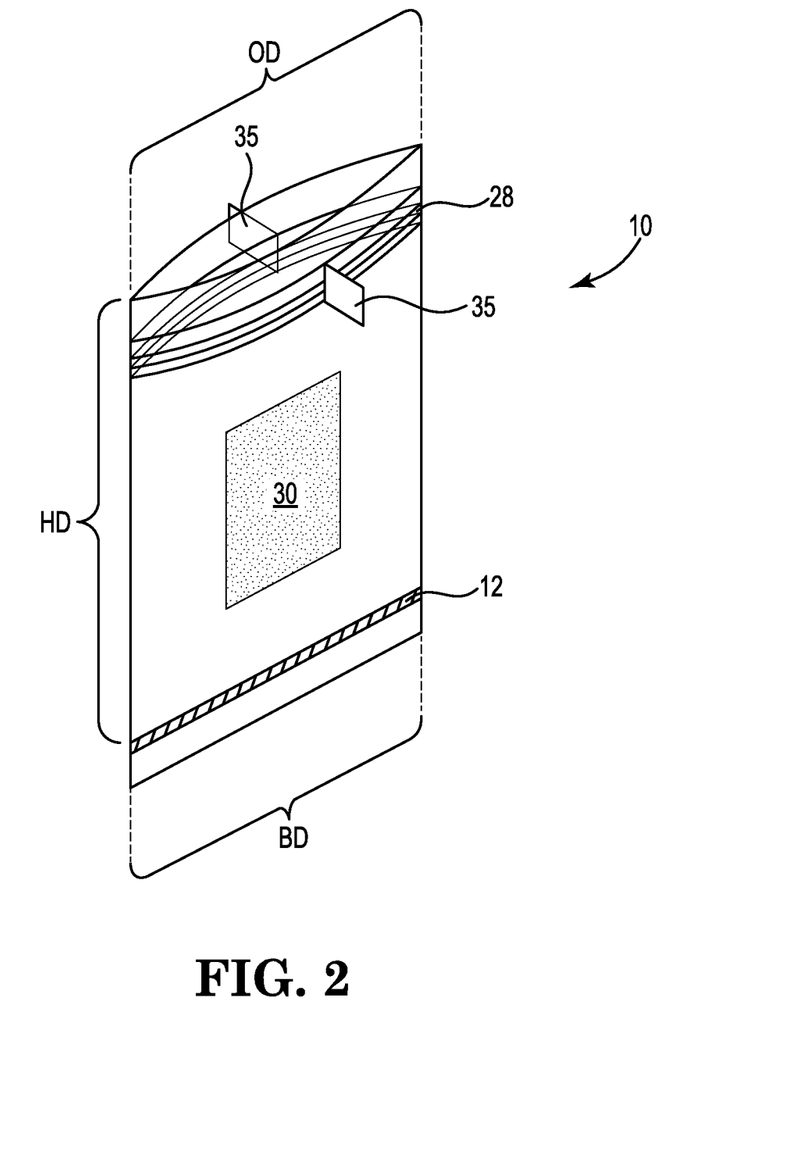
FIG. 2 is a perspective view of an aspect of a bag of the present invention wherein the top seal has been removed.
Figure 3:
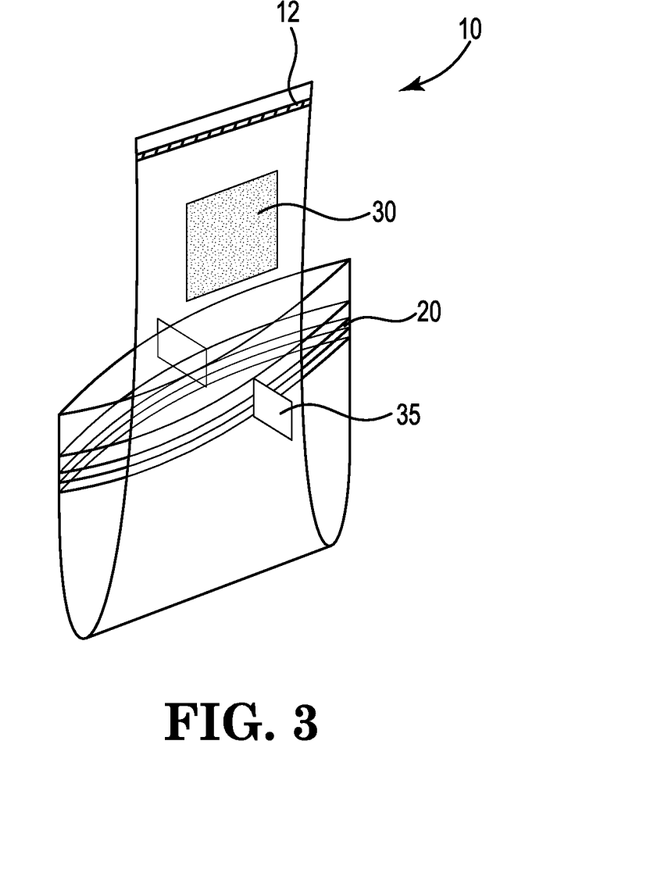
FIG. 3 is a perspective view of the bag shown in FIG. 2 that has been inverted to expose the sample collection material for collection of samples from food surfaces.

FIGS. 1-3 show perspective views of a bag 10 constructed from a flexible, liquid-impermeable sheet material. In an aspect, the bag is constructed from a tube having a seal, such as a heat seal 12 closing one end of the tube to form a pouch. In an alternative aspect, of the present invention where the bag is constructed from two sheets having seals closing three sides of the sheets to form a pouch. In an aspect, the inside of bag 10 is sterile.

In an aspect, the bag is prepared from a material selected from the group consisting of polyolefins, copolymers of ethylene, substituted olefins, polyester, polycarbonate, polyamide, acrylonitrile, cellulose and polylactic acid. In an aspect, the bag is prepared from a material selected from the group consisting of High Density Polyethylene, Low Density Polyethylene, Linear Low Density Polyethylene and Polypropylene.

In an aspect, the bag is made from a polymeric material having a thickness of from 0.2 mils to 3 mils, or from 0.4 mils to 2.5 mils, or from 1.8 mils to 2.2 mils, or from 1.4 mils to 1.6 mils, or from 0.9 mils to 1.1 mils, or from 0.7 mils to 0.9 mils, or from 0.4 mils to 0.6 mils.

The bag 10 comprises a sealable top opening 20. In an aspect, the bag comprises a closure structure having cooperating interlocking or coupling structures that are engaged together. Such a closure is operated by pressing the opposite sides of the mouth of the bag together. An embodiment of this structure is described in U.S. Pat. No. 5,138,750 to Gundlach et al., the disclosure of which is incorporated herein by reference.

In an aspect, the bag comprises a closure mechanism having a slider. Such a slider, which is slidably coupled to each of the opposite sides of the mouth of the bag, is configured so that as it is slid in one direction, it couples the cooperating interlocking or coupling structures of the mouth of the bag together. In contrast, as the slider is slid in the opposite direction, it uncouples the cooperating interlocking or coupling structures of the mouth of the bag. An embodiment of this structure is described in U.S. Pat. No. 2,810,944 to Sander, the disclosure of which is incorporated herein by reference.

In an aspect, the bag comprises a closure mechanism that is a flap comprising a resealable adhesive on the flap.

Bag 10 is additionally provided with a sample collection material 30 that is secured to an inside surface of the bag 10.

In an aspect, sample collection material 30 is secured to an inside surface of the bag by an adhesive or by heat seal.

In an aspect, sample collection material 30 is an approved food contact material. In an aspect, sample collection material 30 is selected from the group consisting of sponge, cloth or gauze. In an aspect, sample collection material 30 is a porous, soft and compressible material comprising cellulose and optionally further comprising wood pulp and/or vegetal fibers. In an aspect, sample collection material 30 is a cloth sponge. In an aspect, sample collection material 30 is a spunbond olefin polymer. In an aspect, the sample collection material has a surface area available for contact to the surface of a substrate to be sampled of from 4 $cm^2$ to 900 $cm^2$. In an aspect, sample collection material has a surface area available for contact to the surface of a substrate to be sampled of from 9 $cm^2$ to 600 $cm^2$. In an aspect, the sample collection material has a surface area available for contact to the surface of a substrate to be sampled of from 9 $cm^2$ to 120 $cm^2$. In an aspect, the sample collection material selected from a sponge, cloth or gauze material having a weight of from about 1 to about 5 oz. wt. per yard of material. In an aspect, the sample collection material selected from a sponge, cloth or gauze material having a weight of from about 2 to about 3 oz. wt. per yard of material. In an aspect, the sample collection material is a woven material which allows particles to be trapped and also presents a rough surface texture so that, during sampling, bacteria is dislodged from the surface being sampled and retained within the sampling material. In an aspect, the sample collection material is durable so that the material does not fracture or come apart while being rubbed on the surface being sampled.

In an aspect, the sample collection material is in the form of a sheet or layer that is bonded to a portion of the bag. In an aspect, the sample collection material is bonded at a seam that forms the bag. In an aspect, the sample collection material is a plurality of sheets. In an aspect, the sample collection material is a plurality of sheets bonded together to form a bag within the outer bag constructed from the flexible, liquid-impermeable sheet material.

In an aspect, the bag is initially sealed on the top by a removable top seal 26 to provide secure closure of the bag, to assure that the interior of the bag is not contaminated before use. In an aspect, this removable top seal 26 is a heat seal or a line permanent adhesive. In an aspect, the removable top seal is removed by tearing off the top of bag 10 at a line of weakness 28 provided in the bag. Aspects of this structure described in U.S. Pat. No. 5,372,428 to Bruno et al. and U.S. Pat. No. 6,004,032 to Kapperman et al., the disclosures of which are incorporated herein by reference.

After removal of top seal 26 (if present), the bag may be opened for inverting the bag to expose the sample collection material for collection of samples from food surfaces. In an aspect, the bag 10 is provided with side pull-tabs 35 that may be used to pull apart the opening of the bag. The side pull-tabs 35 assist in avoiding contamination of the inside of the bag.

FIG. 3 shows the bag 10 in an inverted configuration bag to expose the sample collection material 30 for collection of samples from food surfaces. Bag 10 is thus of a size large enough to permit inversion of the bag to expose the sample collection material for collection of samples from food surfaces and re-inversion to enclose the sample collection material. In an aspect, bag 10 has a linear opening dimension of from 10 cm to 30 cm, a linear bottom dimension of from 10 cm to 30 cm and a linear height dimension of from 15 cm to 40 cm. In an aspect, bag 10 has a linear opening dimension of from 15 cm to 25 cm, a linear bottom dimension of from 15 cm to 25 cm and a linear height dimension of from 25 cm to 35 cm. In an aspect, bag 10 comprises gussets to form a flat bottom.

In an aspect, the sample collection material is in a bag configuration that is secured to the inside of the bag. In an aspect, the sample collection material bag is secured to an inside surface of the bag.

Figure 4:
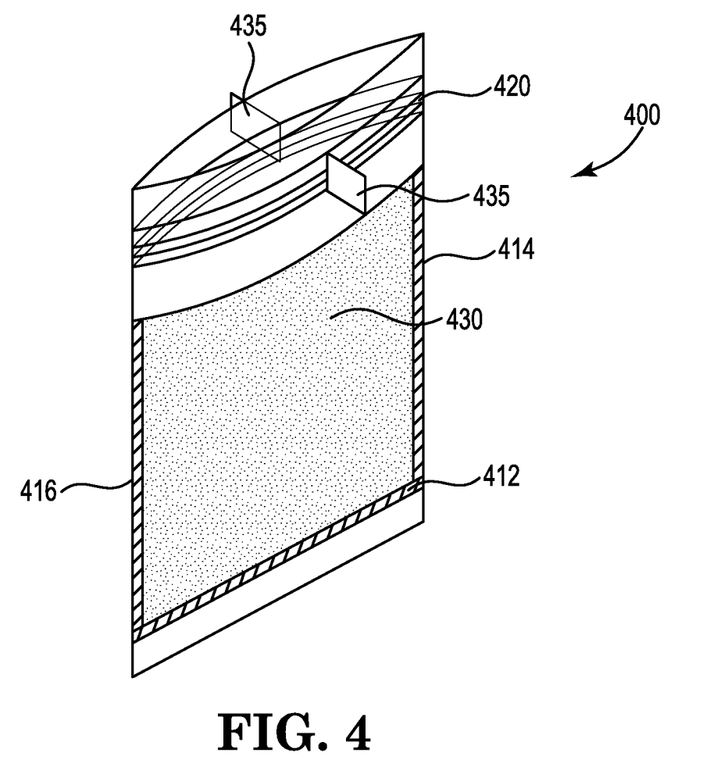
FIG. 4 is a perspective view of an aspect of a bag of the present invention.

FIG. 4 shows a perspective view of bag 400. Bag 400 is provided with sample collection material 430 that is of substantially the same size as one of the walls of bag 400. Sample collection material 430 is secured to the inside of the bag 400 by heat seals 412, 414 and 416, which additionally form the bag 400. In an aspect, sample collection material 430 may additionally or alternatively be secured to an inside surface of the bag by an adhesive or by heat seal that is separate from heat seals 412, 414 and 416. In an aspect, bag 400 is provided with side pull-tabs 435 that may be used to pull apart the opening of the bag. In an aspect, bag 400 comprises a sealable top opening 420 such as described above.

Figure 5:
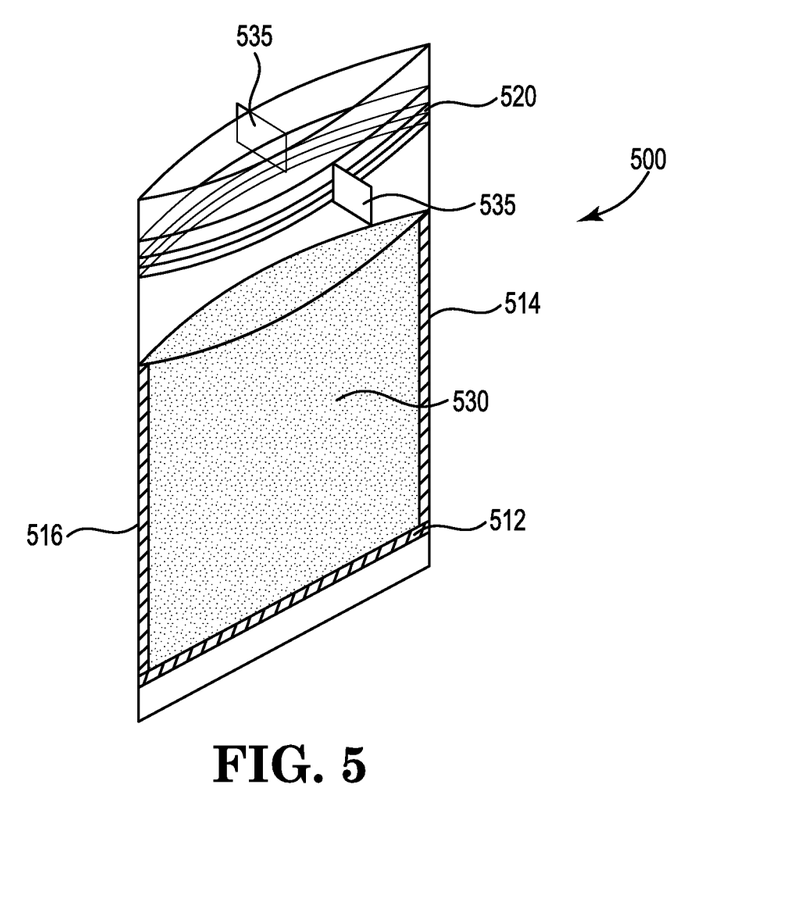
FIG. 5 is a perspective view of an aspect of a bag of the present invention.

FIG. 5 shows a perspective view of bag 500. Bag 500 is provided with sample collection material 530 that is itself a bag constructed of, for example, two sheets material. Sample collection material 530 is secured to the inside of the bag 500 by heat seals 512, 514 and 516, which additionally form the bag 500. In an aspect, sample collection material 530 may additionally or alternatively be secured to an inside surface of the bag by an adhesive or by heat seal that is separate from heat seals 512, 514 and 516. In an aspect, bag 500 is provided with side pull-tabs 535 that may be used to pull apart the opening of the bag. In an aspect, bag 500 comprises a sealable top opening 520 such as described above.

Figure 6:
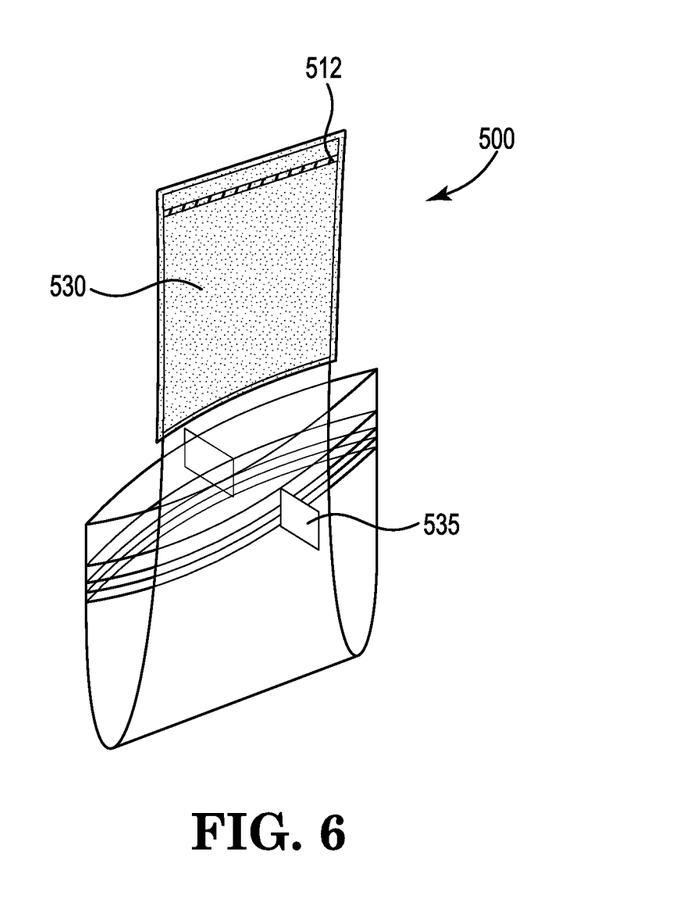
FIG. 6 is a perspective view of the bag shown in FIG. 5 that has been inverted to expose the sample collection material for collection of samples from food surfaces.

FIG. 6 is a perspective view of the bag shown in FIG. 5 that has been inverted to expose the sample collection material for collection of samples from food surfaces. Bag 500 is thus of a size large enough to permit inversion of the bag to expose the sample collection material for collection of samples from food surfaces and re-inversion to enclose the sample collection material. When bag 500 is inverted, sample collection material 530 likewise is inverted and encases the inverted surfaces of bag 500. A large surface area of sample collection material 530 is therefore advantageously available for contact to surfaces to be sampled. In aspects, the user may rotate the inverted bag to use both sides of the available sample collection material 530 for sampling.

Figure 7:
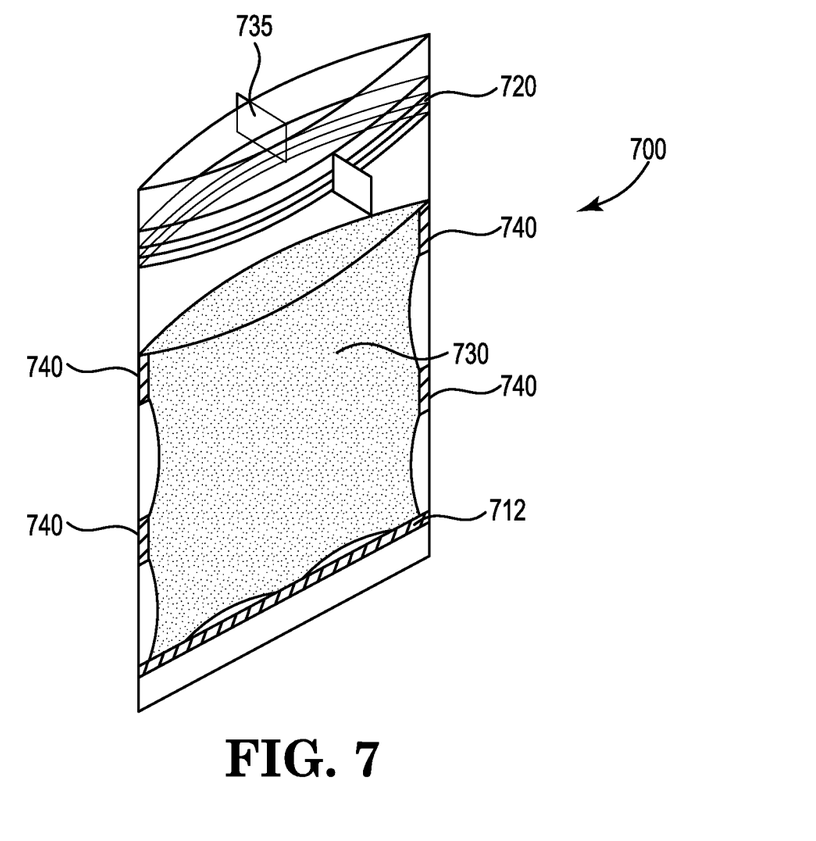
FIG. 7 is a perspective view of an aspect of a bag of the present invention.

FIG. 7 shows a perspective view of bag 700. Bag 700 is provided with sample collection material 730 that is itself a bag constructed of, for example, two sheets material. Sample collection material 730 is secured to the inside of the bag 700 at a number of points by bottom heat seal 712 and side heat seals 740. In an aspect, sample collection material 730 may additionally or alternatively be secured to an inside surface of the bag by an adhesive or by heat seal that is separate from bottom heat seal 712 and side heat seals 740. In an aspect, bag 700 is provided with side pull-tabs 735 that may be used to pull apart the opening of the bag. In an aspect, bag 700 comprises a sealable top opening 720 such as described above.

A method for sampling food products for detection of pathogens, microbial contaminants and/or constituents in products or on surfaces is additionally contemplated, comprising providing the apparatus as described herein; inverting the bag to expose the sample collection material; contacting at least one surface and collecting samples on the sample collection material; re-inverting the bag to enclose the sample collection material; and sealing the bag.

In an aspect, the sampling is carried out on a food product. The food sample may advantageously be sampled at any stage of processing or at any state of preparation for shipping. In an aspect, the food product is sampled at a stationary phase of processing. In an aspect, the food product is being transported on a conveyor belt at the time of collection of sampling. In an aspect, the food product is sampled when in the final package just before closure of the package. In an aspect, the food product being sampled comprises meat.

A method for sampling surfaces for detection of pathogens, microbial contaminants and/or constituents on the surface is additionally contemplated, comprising providing the apparatus as described herein; inverting the bag to expose the sample collection material; contacting at least one surface and collecting food material samples on the sample collection material; re-inverting the bag to enclose the sample collection material; and sealing the bag. In an aspect, the surface is a food preparation surface, such as a counter. In an aspect, the surface is a food conveying surface. In an aspect, the surface is a food storage surface. In an aspect, the surface is a surface on a piece of equipment. In an aspect, the surface is floor. In an aspect, the surface is a wall.

In an aspect, the sample collection is conducted by a person who places their hand in the inverted bag to facilitate the contacting of at least one food surface of a food product.

Advantageously, the sample collection may be carried out with a minimum of disruption of product production and product destruction. Additionally, the present apparatus and method permits spot analysis of any aspect of the production on a controlled basis, because of the portability and selectivity of the sampling process.

After sample collection, the samples are evaluated as appropriate to identify the pathogen or impurity to be checked for using techniques known in the art. Such techniques include culturing and incubating samples to provide materials in amount and form suitable for testing and detection of the material to be identified.

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. Examples of such limitations include preparing the sample in a wet versus a dry environment, different instruments, variations in sample height, and differing requirements in signal-to-noise ratios. For example, "about" can mean greater or lesser than the value or range of values stated by 1/10 of the stated values, but is not intended to limit any value or range of values to only this broader definition. For instance, a concentration value of about 30% means a concentration between 27% and 33%. Each value or range of values preceded by the term "about" is also intended to encompass the embodiment of the stated absolute value or range of values. Alternatively, particularly with respect to biological systems or processes, the term can mean within an order of magnitude, preferably within 5-fold, and more preferably within 2-fold, of a value.

Throughout this specification and claims, unless the context requires otherwise, the word "comprise", and variations such as "comprises" and "comprising", will be understood to imply the inclusion of a stated integer or step or group of integers or steps but not the exclusion of any other integer or step or group of integer or step. When used herein "consisting of" excludes any element, step, or ingredient not specified in the claim element. When used herein, "consisting essentially of" does not exclude materials or steps that do not materially affect the basic and novel characteristics of the claim. In the present disclosure of various embodiments, any of the terms "comprising", "consisting essentially of" and "consisting of" used in the description of an embodiment may be replaced with either of the other two terms.

All patents, patent applications (including provisional applications), and publications cited herein are incorporated by reference as if individually incorporated for all purposes. Unless otherwise indicated, all parts and percentages are by weight and all molecular weights are weight average molecular weights. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. An apparatus for sampling food products and/or surfaces comprising,
   a bag constructed from a flexible, liquid-impermeable sheet material,
   the bag comprising a sealable top opening and a sample collection material, wherein the sample collection material is in a bag configuration that is secured to an inside surface of the bag,
   the bag being of a size large enough to permit inversion of the bag to expose the sample collection material for collection of samples from surfaces and re-inversion to enclose the sample collection material.

2. The apparatus of claim 1, wherein the bag is further provided with a removable top seal external to the sealable top opening.

3. The apparatus of claim 2, wherein the removable top seal is removed by tearing the bag at a line of weakness provided in the bag.

4. The apparatus of claim 1, wherein the sample collection material is selected from the group consisting of sponge, cloth or gauze.

5. The apparatus of claim 1, wherein the sample collection material is a porous, soft and compressible material comprising cellulose.

6. The apparatus of claim 1, wherein the sample collection material has a surface area available for contact to the surface of a substrate to be sampled of from 4 $cm^2$ to 900 $cm^2$.

7. The apparatus of claim 1, wherein the sample collection material has a weight of from about 1 to about 5 oz. wt. per yard of material.

8. The apparatus of claim 1, wherein the flexible liquid-impermeable sheet material is selected from the group consisting of polyolefins, copolymers of ethylene, substituted olefins, polyester, polycarbonate, polyamide, acrylonitrile, cellulose and polylactic acid.

9. The apparatus of claim 1, wherein the flexible liquid-impermeable sheet material is selected from the group consisting of High Density Polyethylene, Low Density Polyethylene, Linear Low Density Polyethylene and Polypropylene.

10. The apparatus of claim 1, wherein the bag has a linear opening dimension of from 10 cm to 25 cm, a linear bottom dimension of from 10 cm to 25 cm and a linear height dimension of from 15 cm to 30 cm.

11. The apparatus of claim 1, wherein the bag comprises gussets to form a flat bottom.

12. The apparatus of claim 1, wherein the bag is made from a polymeric material having a thickness of from 0.2 mils to 3.

13. The apparatus of claim 1, wherein the bag comprises laterally extending tabs proximate to the opening positioned to assist in opening the bag for inversion.

14. The apparatus of claim 1, wherein the inside of the bag is sterile.

15. A method for sampling food products and/or surfaces for detection of pathogens, microbial contaminants and/or constituents in food products and/or on surfaces, comprising
   providing the apparatus of claim 1;
   inverting the bag to expose the sample collection material;
   contacting at least one surface and collecting material samples on the sample collection material;
   re-inverting the bag to enclose the sample collection material; and sealing the bag.

16. The method of claim 15 wherein the sampling is carried out on a food product.

* * * * *

UNITED STATES PATENT AND TRADEMARK OFFICE
CERTIFICATE OF CORRECTION

| | | |
|---|---|---|
| PATENT NO. | : 11,680,873 B2 | Page 1 of 1 |
| APPLICATION NO. | : 16/756942 | |
| DATED | : June 20, 2023 | |
| INVENTOR(S) | : Ted Brown et al. | |

It is certified that error appears in the above-identified patent and that said Letters Patent is hereby corrected as shown below:

In the Claims

In Column 7, Line 3, in Claim 12, delete "3." and insert -- 3 mils. --, therefor.

Signed and Sealed this
Twenty-ninth Day of August, 2023

*Katherine Kelly Vidal*

Katherine Kelly Vidal
*Director of the United States Patent and Trademark Office*